United States Patent [19]
Tiffin et al.

[11] Patent Number: 5,742,658
[45] Date of Patent: Apr. 21, 1998

[54] APPARATUS AND METHOD FOR DETERMINING THE ELEMENTAL COMPOSITIONS AND RELATIVE LOCATIONS OF PARTICLES ON THE SURFACE OF A SEMICONDUCTOR WAFER

[75] Inventors: Donald A. Tiffin; Tim Z. Hossain, both of Austin, Tex.

[73] Assignee: Advanced Micro Devices, Inc., Sunnyvale, Calif.

[21] Appl. No.: 653,727

[22] Filed: May 23, 1996

[51] Int. Cl.$^6$ ........................................ G01T 1/36
[52] U.S. Cl. ........................... 378/44; 378/45; 378/49
[58] Field of Search ............................ 378/44, 45, 46, 378/48, 49, 50, 84

[56] References Cited

U.S. PATENT DOCUMENTS

| | | | |
|---|---|---|---|
| 3,859,525 | 1/1975 | Ashe et al. | 378/45 |
| 4,131,794 | 12/1978 | Bruninx | 378/49 |
| 4,764,945 | 8/1988 | Tadahiro | 378/44 X |
| 4,819,256 | 4/1989 | Annis et al. | 378/44 X |
| 5,220,591 | 6/1993 | Ohsugi et al. | 378/44 X |
| 5,325,416 | 6/1994 | Saito et al. | 378/44 X |
| 5,430,786 | 7/1995 | Komatsu et al. | 378/45 |
| 5,537,451 | 7/1996 | Serebryakov et al. | 378/44 X |

OTHER PUBLICATIONS

Nomura, et al. "Advances in X-Ray Analysis", (1989) vol. 32, pp. 205–210.
Kosonocky, et al. "Electron. Des.", (Apr. 12, 1975), vol. 23, pp. 58–63.
Janesick, et al. "Optical Engineering", (Aug., 1987), vol. 26, No. 8, pp. 692–714.
Bower, "CCD–Solid State Imaging Technology", (1982 Catalog), pp. 121–125.
Amelio "CCD–Solid State Imaging Technology", (1982 Catalog), pp. 126–137.

*Primary Examiner*—David P. Porta
*Attorney, Agent, or Firm*—Kevin L. Daffer; Conley, Rose & Tayon

[57] ABSTRACT

An apparatus and method are presented for determining the elemental compositions and relative locations of particles on a surface of a semiconductor wafer. An exposed region of the surface of the semiconductor wafer is subjected to a beam of primary X-ray photons, and secondary X-ray photons emitted by atoms of elements on and just under the surface of the semiconductor wafer are detected by an X-ray detector array which includes multiple X-ray detectors. Each X-ray detector produces an output signal which is proportional to energy levels of incident X-ray photons. The X-ray detectors are laterally displaced from one another, and arranged to allow two-dimensional resolution of detected secondary X-ray photons emitted by atoms of elements on the surface of the semiconductor wafer. The X-ray detector array is preferably an electronic area image sensor including a two-dimensional array of photosensor elements formed upon a monolithic semiconductor substrate. With adequate resolution, the X-ray detector array may also provide information as to the relative sizes of particles on the surface of the semiconductor wafer. By virtue of an employed total reflection X-ray fluorescence (TXRF) technique, substantially all of the detected X-ray photons are secondary X-ray photons emitted by atoms of elements located on and just under the exposed surface of the semiconductor wafer.

28 Claims, 11 Drawing Sheets

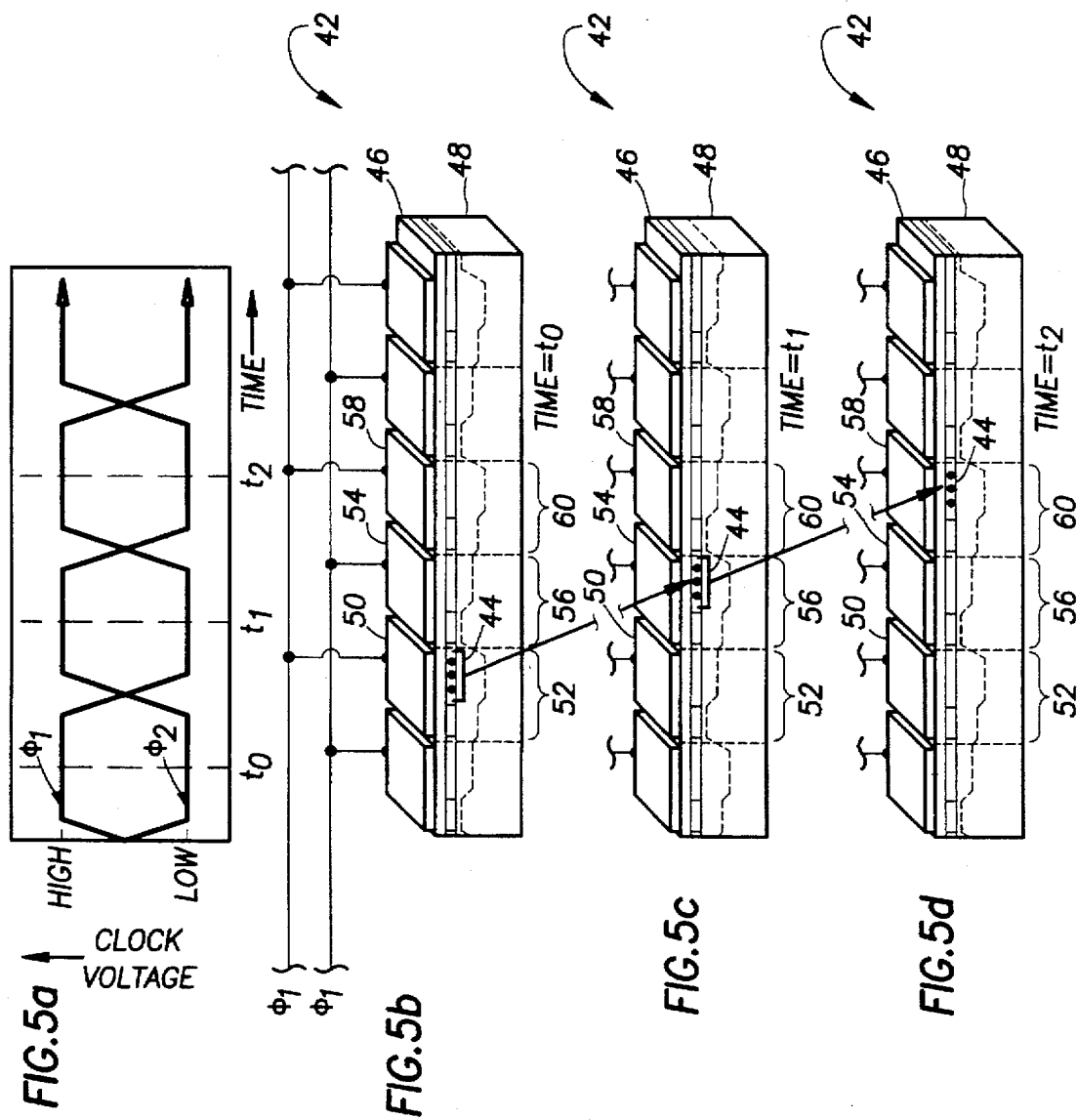

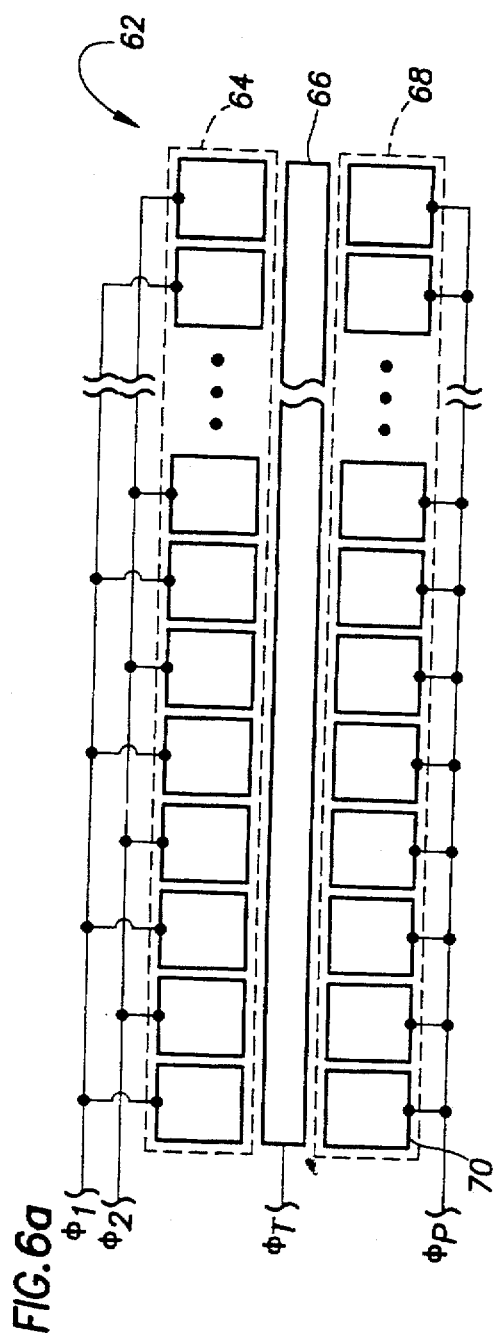
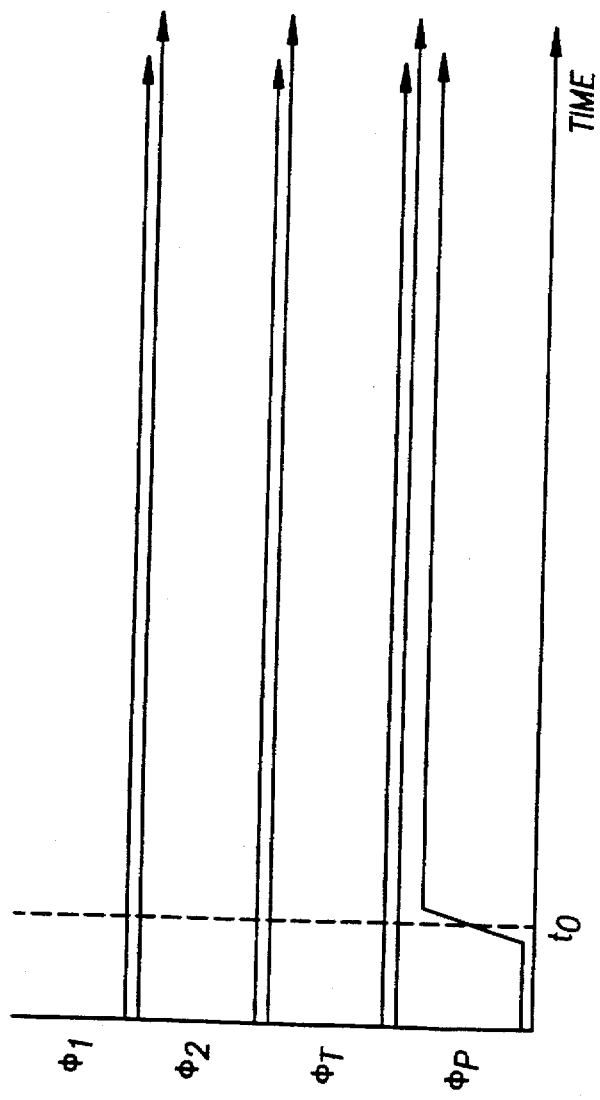
FIG. 6a
FIG. 6b

APPARATUS AND METHOD FOR DETERMINING THE ELEMENTAL COMPOSITIONS AND RELATIVE LOCATIONS OF PARTICLES ON THE SURFACE OF A SEMICONDUCTOR WAFER

BACKGROUND OF THE INVENTION

1. Field of the Invention

This invention relates to integrated circuit manufacturing and more particularly to detecting and determining the elemental compositions of particulate contaminants located on the surface of a semiconductor wafer.

2. Description of the Relevant Art

Scrupulously clean wafers are critical for obtaining high yields in the manufacture of integrated circuits with submicron device dimensions. The small feature sizes and the thinnesses of layers deposited on the surfaces of semiconductor wafers during the manufacture of such devices makes the process extremely vulnerable to damage caused by surface contaminants. Failure to detect and remove surface contaminants during manufacture may degrade the performances or reliabilities of produced devices, and may even render a significant number of devices formed upon contaminated surfaces of semiconductor wafers inoperative.

The two general categories of semiconductor wafer surface contaminants are particulates and films. Particulates are any tiny pieces (i.e., particles) of foreign material that have readily discernible boundaries. Sources of particulate contamination include dust in the air, lint from clothing worn by clean room personnel, particles present in processing chemicals, and particles generated by processing equipment. Film contaminants form layers of foreign material on surfaces of a semiconductor wafers. Examples of film contaminants include solvent residues, photoresist developer residue, oil films, and metallic films deposited during procedures involving immersion of wafers in a liquid.

In order to produce devices with acceptable performance and reliability characteristics, detection of surface contaminants during wafer processing must occur. Common diagnostic techniques used to determine physical properties of wafer surfaces and device structures formed thereupon include optical microscopy, scanning electron microscopy (SEM), and transmission electron microscopy (TEM). Optical microscopy is effectively used to detect particulates down to about 0.1 microns in diameter, as well as the presence of scratches and solvent residues on wafer surfaces. A scanning electron microscope directs a beam of primary electrons at the surface of a wafer and detects emitted secondary electrons in order to form an image of the wafer surface. Production compatible scanning electron microscopes, which operate at energy levels low enough to prevent damage to device structures, are capable of resolutions in the 20–30 angstrom range. TEM also uses an incident electron beam in order to form an image of a wafer surface, and TEM is capable of resolutions on the order of 2 angstroms. The energies of electrons used in TEM are high enough to cause damage to device structures, however, thus TEM analysis cannot be performed on production wafers.

Once the presence of a surface contaminant is detected, it may be possible to remove the contaminant using a cleaning procedure. Cleaning procedures are not totally effective, however, and represent additional processing steps which pose an additional source of contamination. Identifying and eliminating a source of contamination before contamination occurs is thus preferred. In order to ascertain where contaminants come from, it is often necessary to examine product wafers (i.e., wafers expected to yield operational devices) before and after each processing step. Having the ability to examine product wafers for contaminants at various processing stages without damaging the wafers during the examination is a challenge. If product wafers can be so monitored, however, dedicated test wafers are not needed. Test wafers, typically included in every grouping of wafers and processed just like the production wafers they accompany, represent a reduction in manufacturing yield as they do not produce marketable operational devices.

In order to identify the source of a contaminant, it is useful to know the elemental composition and physical attributes of the contaminant. Diagnostic techniques commonly used for elemental analysis include Auger emission spectroscopy (AES), secondary ion mass spectroscopy (SIMS), and X-ray fluorescence spectroscopy (XRF). Like SEM techniques, AES techniques involve directing a beam of primary electrons at the surface of a wafer. Instead of forming an image using detected secondary electrons emitted by atoms on the upper surface of a wafer, AES techniques measure the energy levels of the emitted electrons to determine elemental compositions of surface structures. Scanning electron microscopes with added equipment to accomplish elemental analysis using AES techniques are available. However, scanning electron microscopes so configured are not only expensive to own and operate, they are also not capable of rapid systematic scanning of wafers required for routine in-line wafer examination. SIMS techniques analyze small pieces of materials dislodged from wafer surfaces by ion bombardment, and are thus destructive in nature and are not suitable for in-line examination of processed wafers.

In XRF techniques, a beam of primary X-rays is directed at the surface of a semiconductor wafer, and the energy levels (or corresponding wavelengths) of resultant secondary X-rays emitted by atoms of elements on and just under the surface of the wafer are measured. Atoms of elements in target materials emit secondary X-rays with uniquely characteristic energy levels (or corresponding wavelengths). Thus the elemental compositions of materials on and just under the surface of the wafer may be determined from the measured energy levels (or wavelengths) of emitted secondary X-rays. XRF techniques offer rapid, non-destructive determination of elemental composition down to trace quantities over a wide range of elements with no sample preparation, and is thus a highly desirable tool for in-line product wafer examination.

There are two main types of XRF techniques, wavelength-dispersive XRF (WDXRF) and energy-dispersive XRF (EDXRF). In WDXRF techniques, a sample is irradiated with polychromatic primary X-rays (i.e., primary X-rays with many different wavelengths), resultant secondary X-rays are dispersed by diffraction into discrete wavelengths, and intensities of the secondary X-ray photons are measured versus wavelength. Elemental coverage using WDXRF techniques typically can be extended down %o boron when analysis is carried out in a vacuum. EDXRF techniques involve irradiating a sample with polychromatic primary X-rays and measuring fluorescent secondary X-ray intensity versus detected secondary X-ray photon energy level. Elemental coverage with commercially-available equipment employing EDXRF techniques typically extends down to sodium.

A primary X-ray photon incident upon a target material may be absorbed or scattered. Characteristic secondary X-ray photons are emitted only when primary X-ray photons are absorbed. Primary X-ray photons may loose energy when scattered by atoms of the target material. Such scattered primary X-ray photons which reach the X-ray detector of an XRF instrument create an unwanted background intensity level which secondary X-ray photons must exceed in order to be discerned. Thus the smallest amount of an element which may be detected in a sample using an XRF instrument is largely determined by the background intensity level at the energy level (or corresponding wavelength) associated with characteristic secondary X-rays emitted by that element. The sensitivity of an XRF instrument is thus largely dependent upon the background intensity level, and the sensitivity of an XRF instrument may be improved by reducing the amount of scattered primary X-rays reaching the detector.

A relatively new EDXRF surface analysis technique known as total reflection X-ray fluorescence (TXRF) is ideally suited for the examination of semiconductor wafers and other materials with substantially flat surfaces. In TXRF, an angle of incidence formed between an incident primary X-ray beam and a substantially flat sample surface is very small, typically less than 0.2 degree. At such small angles of incidence, almost all of the primary X-ray photons striking the sample surface are reflected away from the surface. Primary X-ray photons are also reflected away from an X-ray detector positioned over the region of the wafer surface where the primary X-ray beam impacts the wafer surface. The number of scattered primary X-rays reaching the detector is thus significantly reduced. As a result, surface analysis instruments employing TXRF techniques have reduced background intensity levels over other types of XRF analysis instruments. Smaller quantities of elements may be detected with TXRF instruments due to their greater sensitivities.

Although XRF techniques are capable of rapid and non-destructive determinations of elemental compositions, typical XRF instruments have characteristics which limit their usefulness in identifying the source of particle contamination on the surface of a silicon wafer. One limiting characteristic is that they illuminate a relatively large exposed region on the surface of the wafer. A second limiting characteristic is that they employ a single X-ray detector to detect secondary X-ray photons from atoms of elements located in the exposed region. While it may be possible to detect secondary X-ray photons emitted by atoms of two different elements, it is not possible to tell if these atoms are present within a single particle or within two or more particles located in the exposed region. Thus it not possible to determine the number, relative sizes, or even the relative locations of particles within the exposed region.

No known surface analysis technique is capable of providing a fast, non-destructive, and cost-effective approach to identifying the source of particle contamination on the surface of a silicon wafer. It would thus be desirable to develop a surface analysis technique which employs a rapid, non-destructive TXRF elemental identification technique and the position resolving capability of an array of X-ray detectors. Such a surface analysis technique would be capable of determining the elemental compositions and relative locations of particles on a surface of a semiconductor wafer. Many X-ray detectors may be employed, each positioned to detect secondary X-ray photons emitted by atoms of elements located within a selected portion of a surface region exposed to primary X-ray photons. In this case, the desired surface analysis technique may also be capable of providing valuable information as to number and relative sizes of particles on the surface of the semiconductor wafer.

SUMMARY OF THE INVENTION

The problems outlined above are in large part solved by an apparatus and method for determining the elemental compositions and relative locations of contaminant particles located upon a surface of a semiconductor wafer. A region of the surface of the semiconductor wafer is subjected to beam of primary X-ray photons, and secondary X-ray photons emitted by atoms of elements on and just under the surface of the semiconductor wafer are detected by an X-ray detector array including multiple laterally-displaced X-ray detectors. Each of the X-ray detectors produces an output signal which is proportional to the energy levels of incident X-ray photons. The X-ray detectors are laterally displaced from one another, and arranged to allow two-dimensional resolution of detected secondary X-ray photons emitted by atoms of elements present in contaminant particles located on the surface of the semiconductor wafer. The X-ray detector array is preferably an electronic area image sensor including a two-dimensional array of photosensor elements formed upon a monolithic semiconductor substrate. With a large number of photosensor elements (i.e., adequate resolution), the X-ray detector array may also provide information as to the number and relative sizes of particles on the surface of the semiconductor wafer, By virtue of an employed TXRF technique, the majority of the detected X-ray photons are secondary X-ray photons emitted by atoms of elements located on and just under the exposed surface of the semiconductor wafer. The number of scattered primary X-ray photons detected is substantially reduced over more common XRF techniques.

An exemplary embodiment of the present apparatus includes a high-power X-ray source producing a beam of polychromatic primary X-ray photons. The X-ray source may include a rotating anode for increased primary excitation intensity. A multilayer monochromator is aligned to receive the beam of polychromatic primary X-ray photons, and produces a beam of monochromatic primary X-ray photons. The beam of monochromatic primary X-ray photons is directed at the surface of the semiconductor wafer. Secondary X-ray photons emitted by atoms of elements on and just under the surface of the semiconductor wafer are detected by multiple X-ray detectors forming an array of X-ray detectors. Each of the X-ray detectors produces a detector output signal which is coupled to a computer system. A displacement signal produced by a displacement sensor, reflecting the distance between the surface of the semiconductor wafer and the X-ray detector array, is coupled to a position control unit. The position control unit produces a position control signal which is coupled to a sample stage upon which the semiconductor wafer is placed. The sample stage positions the semiconductor wafer relative to the incident beam of monochromatic primary X-ray photons in response to the position control signal.

The present method includes positioning an array of X-ray detectors adjacent to a region of the surface of the semiconductor wafer exposed to a beam of primary X-ray photons. The output signals produced by X-ray detectors making up the array of X-ray detectors are measured, recorded, and converted to corresponding energy levels of detected X-ray photons. A histogram representing the frequency distribution of the energy levels of detected X-ray photons is formed. Characteristic energy levels corresponding to peaks in the histogram are used to identify elemental compositions of particles on the surface of the semiconductor wafer. The recorded output signals and corresponding energy levels are then searched to determine the relative locations of X-ray detectors receiving secondary X-ray photons emitted by identified elements within the array of X-ray detectors. The relative locations of particles on the surface of the semiconductor wafer are then determined by mapping the relative locations of X-ray detectors receiving secondary X-ray photons emitted by identified elements to corresponding locations on the surface of the semiconductor wafer.

BRIEF DESCRIPTION OF THE DRAWINGS

Other objects and advantages of the invention will become apparent upon reading the following detailed description and upon reference to the accompanying drawings in which:

FIG. 5a is a graph of electrical voltage waveforms Φ1 and Φ2 applied to gate electrodes of elements of a transport register versus time in order to move charge packets along the transport register;

FIG. 5b is a perspective view of the transport register with a charge packet stored in a potential well of a first element of the transport register at time t0 as indicated in FIG. 5a;

FIG. 5c is a perspective view of the elements of the transport register at time t1 after the charge packet has moved from the first element to a second element;

FIG. 5d is a perspective view of the elements of the transport register at time t2 after the charge packet has moved from the second element to a third element;

FIG. 6a is a top plan view of a section of an electronic linear imaging device including a transport register, a photogate, and a linear array of photosensor elements;

FIG. 6b is a timing diagram showing a positive voltage being applied to the ΦP signal line of the linear imaging device of FIG. 6a at the start of a photocharge accumulation (i.e., integration) period;

Figure 1:
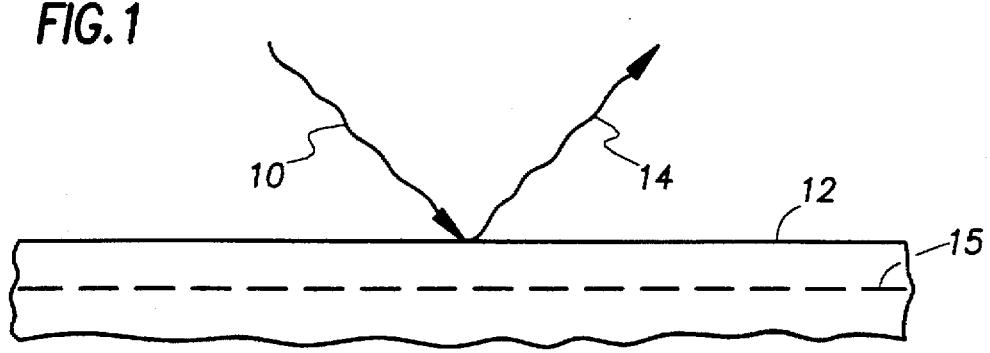
FIG. 1 is a view of a primary X-ray photon incident upon a target material, resulting in the emission of a secondary X-ray photon by the target material.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

Figure 2A:
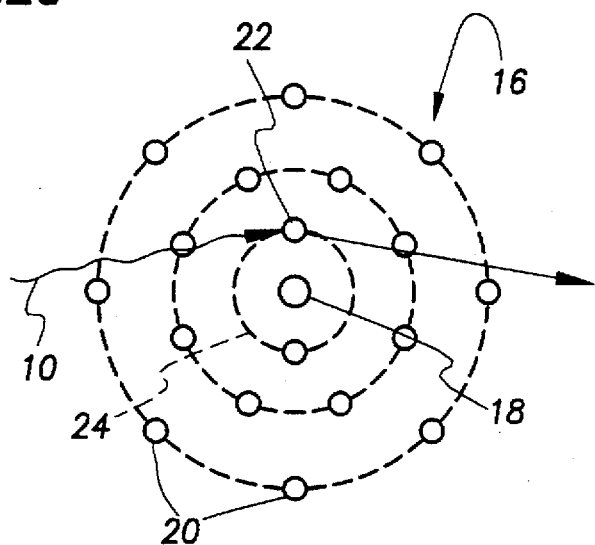
FIG. 2a is a representation of the primary X-ray impacting an atom of an element within the target material of FIG. 1.
Figure 2B:
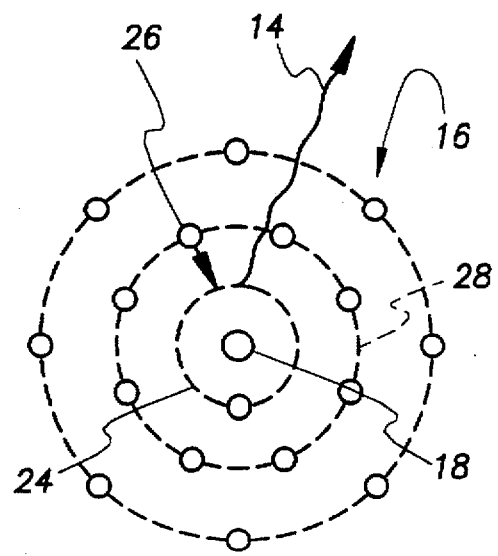
FIG. 2b shows the atom of FIG. 2a emitting a secondary X-ray photon after absorbing the primary X-ray photon.

FIGS. 1, 2a, and 2b will be used to describe in general how XRF occurs within the realm of the present invention. FIG. 1 is a view of a primary X-ray photon 10 incident upon a target material 12, resulting in the emission of a secondary X-ray photon 14 by target material 12. X-ray photon absorption and emission occur at the atomic level. X-ray fluorescence spectrometry permits examination of a target material 12 from the surface of the target material down to a maximum escape depth 15 of secondary X-ray photons.

FIG. 2a includes a representation of an atom 16 of target material 12. In the simple atomic model shown, atom 16 has a nucleus 18 surrounded by electrons 20 at different discrete distances from nucleus 18 called electron shells. A given electron shell has a binding energy level equal to the amount of energy required to remove an electron from the electron shell. The binding energy level of an electron shell is inversely proportional to the distance of the electron shell from the nucleus. The innermost electron shell of an atom is called the K shell, and has the highest binding energy level associated with it. In FIG. 2a, K-shell electron 22 is located in K shell 24.

FIG. 2a also shows primary X-ray photon 10 impacting atom 16 within a target material 12. If the energy level of primary X-ray photon 10 (E) is greater than the binding energy level of a K shell 24 ($\phi_K$) the entire energy of primary X-ray photon 10 is absorbed by atom 16, and one of the electrons in K shell 24 is ejected from atom 16 of target material 12. As depicted in FIG. 2a, K-shell electron 22 is ejected from atom 16 after primary X-ray photon 10 is absorbed by atom 16 of target material 12. K-shell electron 22 is ejected with a kinetic energy of $(E-\phi_K)$.

With a vacancy in K shell 24, atom 16 of target material 12 is energetic and unstable. The most probable stabilization mechanism is the filling of the vacancy in K shell 24 by an electron located in an electron shell with a lower binding energy level. As shown in FIG. 2b, an L-shell electron 26 in L shell 28, farther from nucleus 18 than K shell 24, may fill the vacancy in K shell 24. As L-shell electron 26 fills the vacancy in K shell 24, atom 16 simultaneously emits secondary X-ray photon 14 with energy $(\phi_K - \phi_L)$, where $\phi_L$ is the binding energy level of L shell 28. With a vacancy now in L shell 28, ionized atom 16 of target material 12 is more stable and less energetic. The energy levels (or corresponding wavelengths) of secondary X-rays emitted by atoms of elements in substances on and just under the surface of a target material are uniquely characteristic, allowing the elemental compositions of the substances to be determined.

Figure 3:
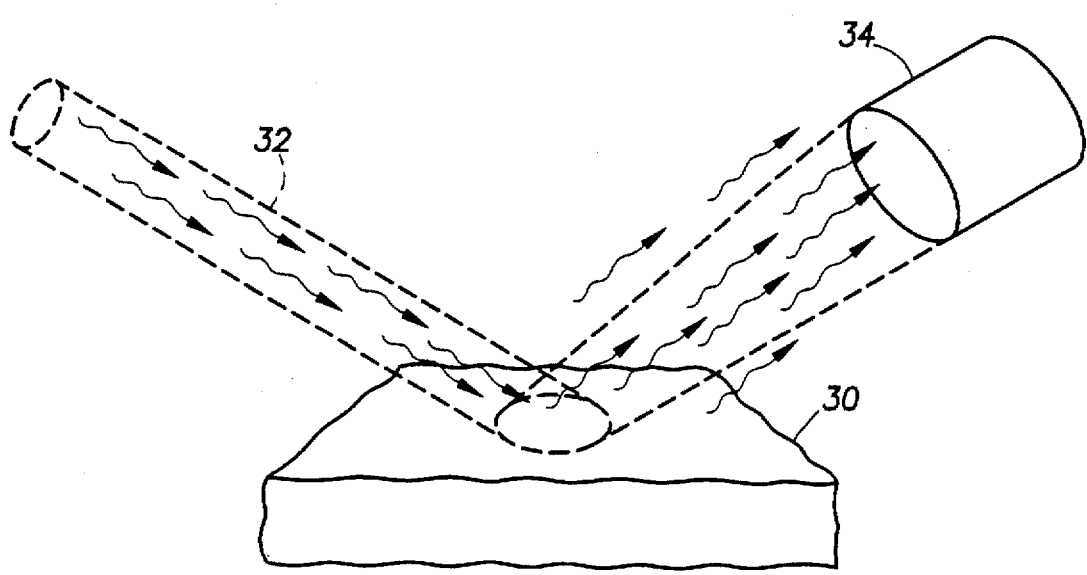
FIG. 3 is a perspective view of a target material undergoing analysis in a typical XRF system.

As mentioned above, primary X-ray photons may be absorbed or scattered by atoms of a target material. Characteristic secondary X-rays are only emitted when incident primary X-rays are absorbed. FIG. 3 is a perspective view of a target material 30 undergoing analysis in a typical XRF system. An incident beam of X-ray photons 32 is directed at an exposed surface of target material 30. An X-ray detector 34 detects both secondary X-ray photons emitted by target material 30 and primary X-ray photons scattered by atoms of the elements comprising target material 30. Primary X-rays which are scattered by atoms of target material 30 rather than absorbed, loose energy in the process, and reach X-ray detector 34 create an unwanted background intensity level which secondary X-ray photons must exceed in order to be discerned.

Figure 4:
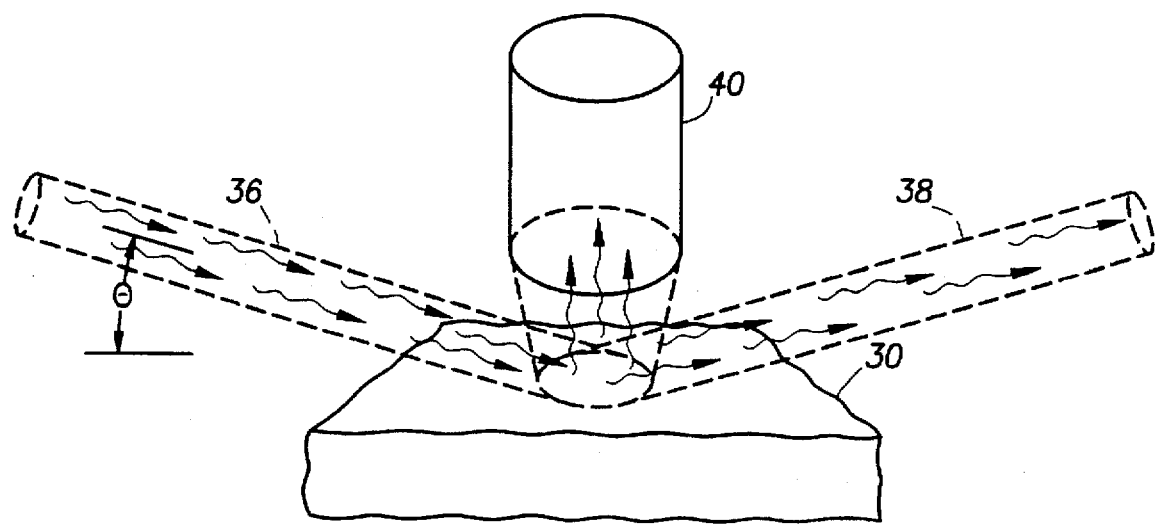
FIG. 4 is a perspective view of a target material undergoing analysis in a TXRF system.

The present invention employs a TXRF analysis technique. As described above, TXRF is an XRF technique which substantially reduces the amount of scattered primary X-rays reaching an X-ray detector. FIG. 4 is a perspective view of target material 30 undergoing analysis in a TXRF system. An angle of incidence θ formed between a beam of primary X-ray photons 36 and an exposed surface of target material 30 is very small, typically less then 0.2 degree. At such angles of incidence, almost all of the photons making up beam of primary X-ray photons 36 and striking the exposed surface are reflected away from the surface, forming a reflected beam of primary X-rays 38. An X-ray detector 40 is positioned directly over and in close proximity to the region of the wafer surface where the beam of primary X-ray photons 36 impacts the surface of target material 30. The number of scattered primary X-rays reaching the detector is significantly reduced, resulting in increased sensitivities of TXRF instruments. Smaller quantities of elements on and just under the exposed surface of target material 30 may be detected with such TXRF instruments due to reduced background intensity levels.

X-ray detectors are key components of XRF instruments. Conventional XRF systems typically use a single X-ray detector optimized for detecting secondary X-ray photons. Electronic area imaging sensors, which include charge-coupled devices (CCDs) and are commonly used in video cameras, are also capable of detecting X-ray photons. Electronic area imaging sensors are manufactured with two-dimensional arrays of photosensitive elements, and the output signals produced by electronic imaging sensors are typically linearly proportional to the energy levels of incident X-ray photons.

When exposed to X-ray photons, electronic area imaging sensors are capable of providing information as to the location within the array where incident X-ray photons were absorbed as well as the energy levels of the incident X-ray photons. An electronic area imaging sensor may thus form a key component of a position-sensitive X-ray detector. The present invention employs an array of photosensitive elements in order to obtain information as to the location within the array where incident X-ray photons were absorbed as well as the energy levels of the incident X-ray photons. As mentioned above, electronic area imaging sensors which include charge-coupled devices (CCDs) are commonly used in video cameras, are also capable of detecting X-ray photons.

A CCD includes closely-spaced metal oxide semiconductor (MOS) capacitors, formed upon a monolithic (i.e., single crystal) substrate, which store and transfer packets of electrical charge. Each MOS capacitor includes a metallic gate electrode positioned over and separated from a planar upper surface of a semiconductor substrate by a layer of an electrical insulating material (typically silicon dioxide, or simply oxide). There are two types of semiconductor substrate materials; n-type and p-type. N-type materials are doped with electron donor impurities, and the majority of the electrical charge carriers present in n-type materials are electrons. P-type materials are doped with electron acceptor impurities, and the majority of the electrical charge carriers present in the material are called "holes". When an electrical potential with sufficient magnitude and the same polarity as the majority carriers in the substrate is applied between the gate electrode and the substrate, majority carriers are electrically repelled from a region of the upper substrate directly under the gate electrode, and minority carriers in the substrate are electrically attracted to the substrate-oxide interface directly under the gate electrode. A region directly under the gate electrode at the substrate-oxide interface represents a minimum energy level for minority carriers, and is called a potential well. A region of the substrate below the potential well and devoid of charge carriers is called the depletion region. CCDs store packets of minority charge carriers in potential wells, and cause these stored charge packets to move by creating new potential wells in locations very near to existing potential wells as the existing potential wells are eliminated.

FIGS. 5a–d illustrate how stored charge packets are transferred from one location to another in CCDs. FIG. 5a is a graph of electrical voltage waveforms Φ1 and Φ2 applied to gate electrodes elements of a transport register 42 versus time. The electrical voltage waveforms shift between a low voltage level and a high voltage level at regular intervals of timed forming clock signals. FIG. 5b is a perspective view of a transport register 42 with a charge packet 44 stored in a potential well of an element 52 of transport register 42 at time t0 as indicated in FIG. 5a. At time t0, a potential well exists under gate electrode 50 of element 52 due to the positive voltage applied to gate electrode 50 (Φ1 in FIG. 5a). As time increases from t0 to t1, a positive voltage is applied to gate electrode 54 of neighboring element 56 (Φ2 in FIG. 5a), and the voltage applied to gate electrode 50 of element 52 is reduced. As a result, a new potential well is created under gate electrode 54 of element 56 as the potential well under gate electrode 50 of element 52 is eliminated. Elements 50 and 54 are located closely enough that charge packet 44 in the collapsing potential well of element 50 responds to the potential well being created under gate electrode 54 by moving to element 56. FIG. 5c is a perspective view of elements of transport register 42 at time t1 after charge packet 44 has moved from element 52 to element 56.

As time increases from t1 to t2 as indicated in FIG. 5a, a positive voltage is applied to gate electrode 58 of element 60 (Φ1 in FIG. 5a) as the voltage applied to gate electrode 54 of element 56 is reduced. As a result, a new potential well is created under gate electrode 58 of element 60 as the potential well under gate electrode 54 of element 56 collapses, and charge packet 44 moves from element 56 to element 60. FIG. 5d is a perspective view of elements of transport register 42 at time t2 after charge packet 44 has moved from element 56 of transport register 42 to element 60.

An electronic linear imaging device employing CCDs includes a linear array of photosensor elements for collecting charges produced by incident electromagnetic radiation in addition to one or more transport registers as described above. FIG. 6a is a top plan view of a section of an electronic linear image device 62 including a transport register 64, a photogate 66, and a linear array of photosensor elements 68. Each element of transport register 64 has a corresponding photosensor element. Clock signals $\Phi 1$ and $\Phi 2$ are used to move charge packets along transport register 64 as described above. A signal $\Phi T$ is coupled to photogate 66, and gate electrodes of all photosensor elements are coupled to a common signal $\Phi P$. Applying a positive voltage to the $\Phi P$ signal line begins a photocharge accumulation or "integration" period during which all minority carriers generated within the confines of the photosensor elements are captured and stored in potential wells formed under the gate electrodes of the photosensor elements. FIG. 6b is a timing diagram showing a positive voltage being applied to the $\Phi P$ signal line at time t0 while the $\Phi 1$, $\Phi 2$, and $\Phi T$ signals are held at a low voltage level.

Figure 6C:
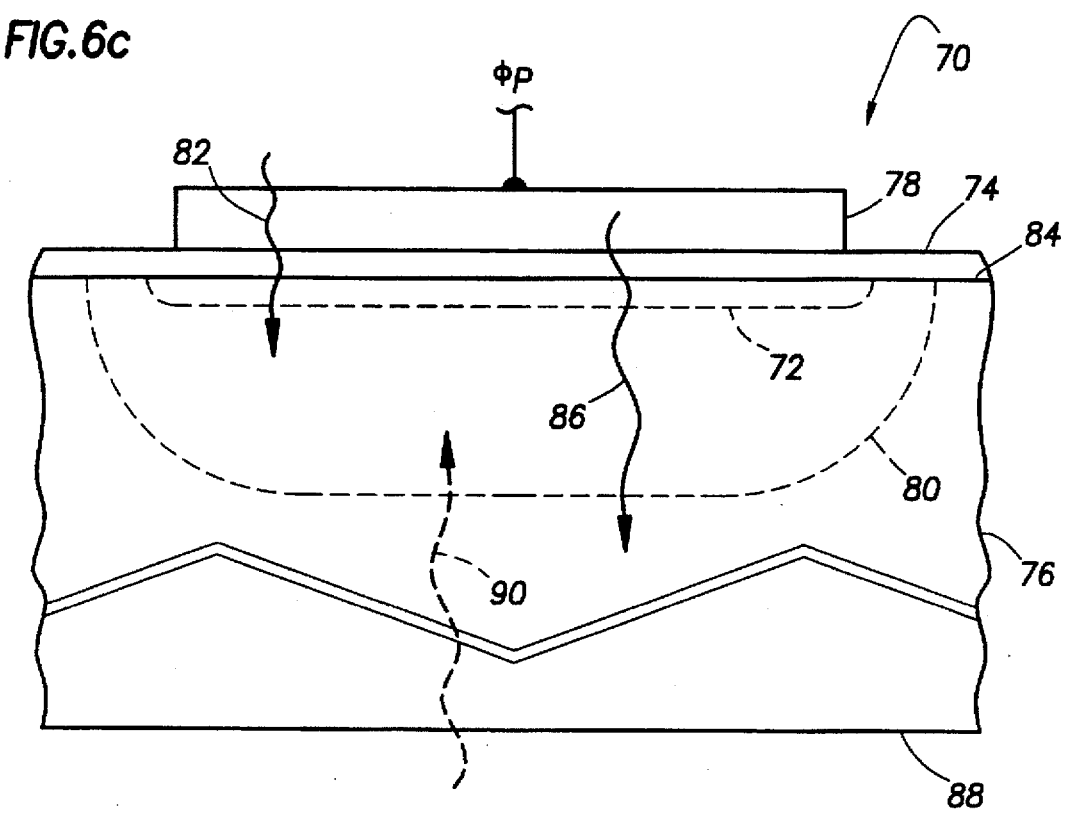
FIG. 6c is a cross-sectional view of primary X-ray photons incident upon a photosensor element of the photosensor array of FIG. 6a during the integration period.

FIG. 6c is a cross-sectional view of photosensor element 70 of photosensor array 68 with a positive voltage signal $\Phi P$ applied to a gate electrode 78. Electrons generated by incident X-ray photons a potential well held in a potential well 72 formed at the interface between an oxide layer 74 and a p-type silicon substrate 76. The periphery of a depletion region 80 defines the extent of the influence of an electromagnetic field, created around gate electrode 78 and penetrating into substrate 76, on electrical charges within substrate 76. An X-ray photon absorbed within silicon substrate 76 creates about 3.65 electron-hole pairs for every electron-volt of energy of the incident X-ray photon. An X-ray photon 82 is shown penetrating gate electrode 78, oxide layer 74, and a frontside surface 84 of substrate 76, before being absorbed within depletion region 80 of silicon substrate 76. Since X-ray photon 82 is absorbed within depletion region 80, the created electrons and holes move under the influence of the electromagnetic field present in depletion region 80. The created holes move away from gate electrode 78 and into an undepleted region of substrate 76 outside of depletion region 80. The created electrons move toward the gate electrode and into potential well 72. Thus electrons created by X-ray photons absorbed in the depletion region of a biased photosensor element are captured and stored in a potential well existing under the gate electrode.

An X-ray photon 86 is shown penetrating gate electrode 78, oxide layer 74, and a frontside surface 84 of substrate 76, before being absorbed in an undepleted region of substrate 76 below depletion region 80. Since X-ray photon 86 is absorbed outside of depletion region 80, the created electrons and holes thermally diffuse into silicon substrate 76. Some of the electrons may recombine with holes in substrate 76. Some of the electrons may drift into depletion region 80 and become captured in photosensor element 70 as they move to potential well 72 under the influence of the electromagnetic field present in depletion region 80. This may not occur before the charge packet in potential well 72 of photosensor element 70 is transferred to a transport register, however. Other created electrons may drift into depletion regions of neighboring photosensor elements and become captured. Thus electrons created by X-ray photons absorbed outside of the depletion region of a given photosensor element may or may not be captured and stored in the potential well of that particular photosensor element. It is therefore necessary to ensure that a majority of the incident X-ray photons are absorbed within the depletion regions of photosensor elements.

X-ray photons with certain energy levels (or corresponding wavelengths) tend to penetrate deeply into silicon substrates before being absorbed. In order to ensure that a majority of such X-ray photons are absorbed within the depletion regions of photosensor elements, a backside surface 88 of silicon substrate 76 may be sufficiently thinned and exposed to such X-ray photons. In FIG. 6c, an X-ray photon 90 enters backside surface 88 and penetrates deeply into silicon substrate 76, but is absorbed within the depletion region of photosensor element 70 due to backside illumination. Frontside illumination of silicon substrate 76 may have resulted in X-ray photon 90 being absorbed below depletion region 80 of photosensor element 70.

Figure 6D:
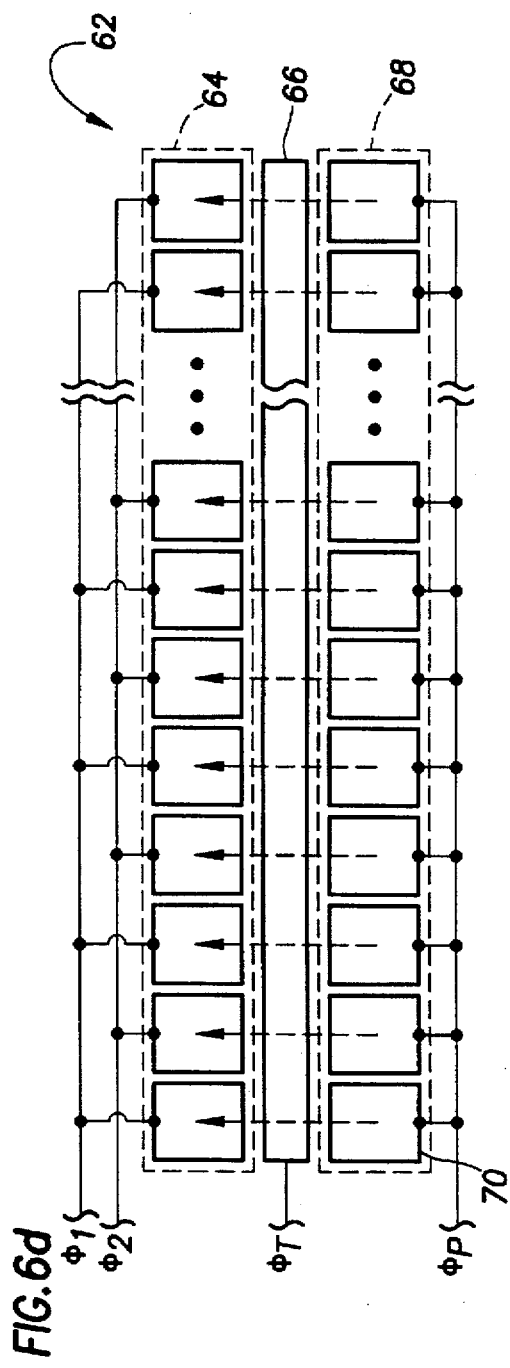
FIG. 6d is a top plan view of the section of the electronic linear imaging device of FIG. 6a illustrating how charge packets are transferred from photosensor elements to corresponding elements of the transport register at the end of the integration period.
Figure 6E:
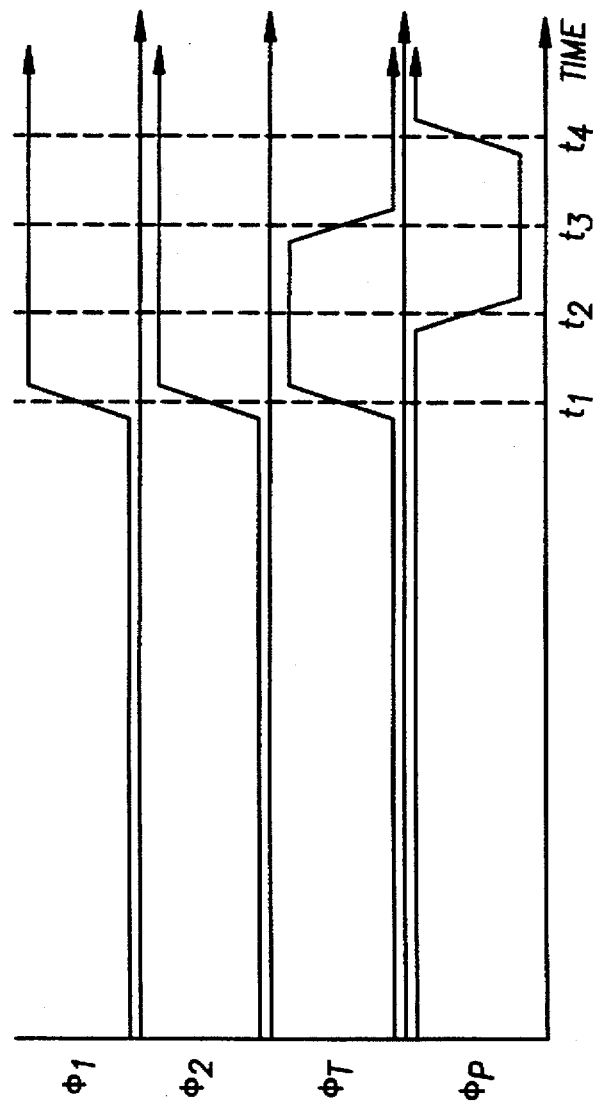
FIG. 6e is a timing diagram showing the signal events which occur at the end of the integration period depicted in FIG. 6d.

FIG. 6d is a top plan view of the section of electronic linear imaging device 62 of FIG. 6a illustrating how charge packets are transferred from photosensor elements to corresponding elements of transport register 64 at the end of an integration period. FIG. 6e is a timing diagram showing the signal events which occur at the end of an integration period. At time t1 in FIG. 6e, a positive voltage is applied to the $\Phi T$ signal line coupled to photogate 66, thus enabling a charge coupling between photosensor elements of photosensor array 68 and the corresponding elements of transport register 64. The voltages applied to the $\Phi 1$ and $\Phi 2$ signal lines, coupled to the gate electrodes of alternating elements of transport register 64, are also increased to a high level, creating potential wells under the gate electrodes of all elements of transport register 64. A very short time later, at time t2, the voltage applied to the $\Phi P$ signal line coupled to the gate electrodes of all photosensor elements of photosensor array 68 is reduced to a low level, causing the potential wells under the gate electrodes of the photosensor elements to collapse. At time t3, the voltage applied to the $\Phi T$ signal line coupled to photogate 66 is also reduced to a low level, thus disabling the charge coupling between corresponding photosensor and transport register elements. As a result, the packets of accumulated photocharge held in the potential wells under the gate electrodes of the photosensor elements transfer from the photosensor elements to the corresponding elements of transport register 64 as the potential wells of the photosensor elements collapse and potential wells develop under the gate electrodes of the elements of transport register 64. At time t4, the voltage applied to the $\Phi P$ signal line may be increased to a high level as shown, again creating potential wells under the gate electrodes of the photosensor elements of photosensor array 68 and beginning another integration period.

Figure 6F:
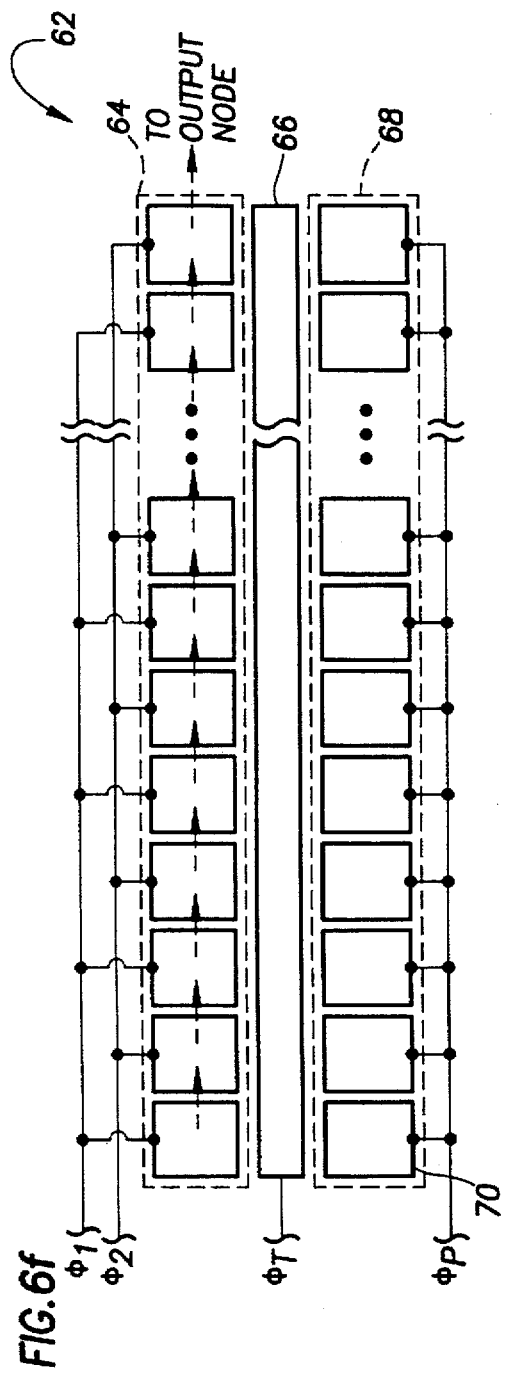
FIG. 6f is a top plan view of the section of the electronic linear imaging device of FIG. 6a illustrating how charge packets are transferred from one element of the transport register to another, enabling the transport of charge packets from individual photosensor elements to a common output node.
Figure 6G:
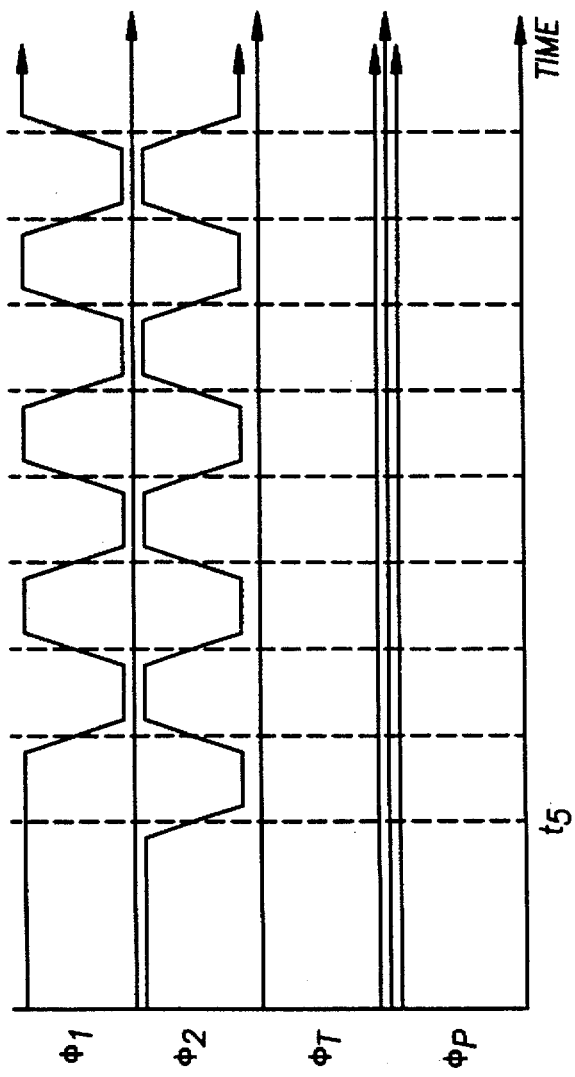
FIG. 6g is a timing diagram showing the signal events which occur during the charge transport mode depicted in FIG. 6f.

FIG. 6f is a top plan view of the section of electronic linear imaging device 62 of FIG. 6a illustrating how charge packets are transferred from one element of transport register 64 to another, enabling the transport of charge packets from individual photosensor elements to a common output node. FIG. 6g is a timing diagram showing the signal events which occur during charge transport. At time t5 in FIG. 6b, alternating clock signal waveforms are applied to the $\Phi 1$ and $\Phi 2$ signal lines coupled to the gate electrodes of the elements of transport register 64, enabling charge coupling between elements of transport register 64. Packets of charge accumulated during the integration period are transported from photosensor elements to a common output node along the chain of elements comprising the transport register as described above. The voltage applied the $\Phi T$ signal line remains low, and charge coupling between photosensor elements and corresponding elements of transport register 64 remains disabled during charge transport. The voltage applied to the $\Phi P$ signal line remains at a high level, and photocharges continue to accumulate in potential wells under the gate electrodes of the photosensor elements of photosensor array 68.

Figure 7:
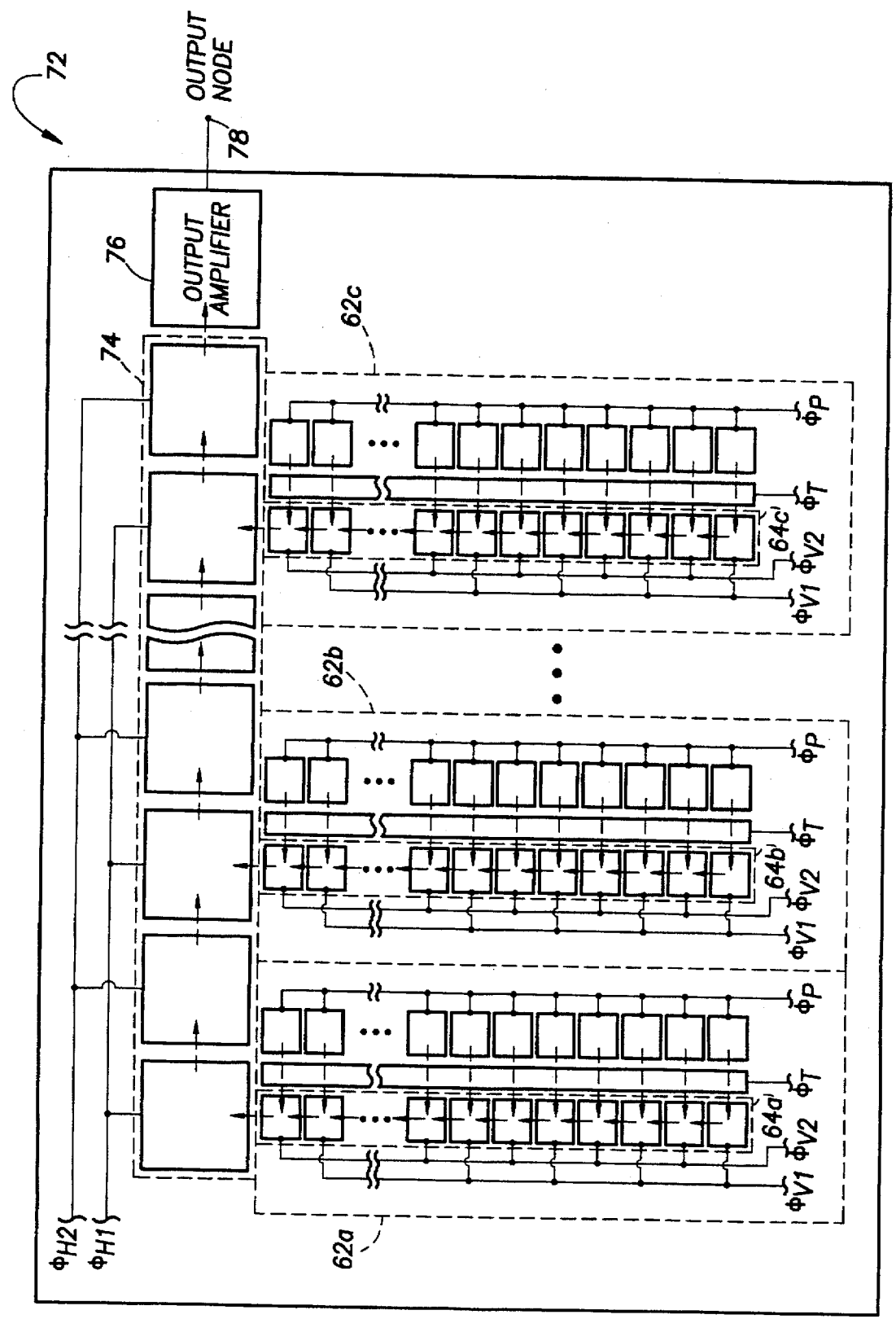
FIG. 7 is a top plan view of a representative embodiment of an electronic area image sensor including a two-dimensional array of photosensor elements.

Multiple linear sections 62 may be arranged to form a two-dimensional array of photosensor elements. Such a two-dimensional photosensor array is called an area image sensor. FIG. 7 is a top plan view of a representative embodiment of an electronic area image sensor 72. In FIG. 7, each of the linear sections 62*a*, 62*b*, and 62*c* are copies of linear section 62 described above. Elements of vertical transport registers 64*a–c* of linear sections 62*a–c*, respectively, are coupled to a first set of clock signals ΦV1 and ΦV2. A terminal element of each vertical transport register is coupled to an element of a horizontal transport register 74. Elements of horizontal transport register 74 are coupled to a second set of clock signals ΦH1 and ΦH2. The two sets of clock signals may be coordinated to transport accumulated charge packets from individual photosensor elements of each linear section to an input terminal of an output amplifier 76. Output amplifier 76 produces an output voltage signal which is linearly proportional to the magnitude of the charge contained in a charge packet arriving at the input terminal, and drives output node 78 with the linearly proportional output voltage signal.

Figure 8:
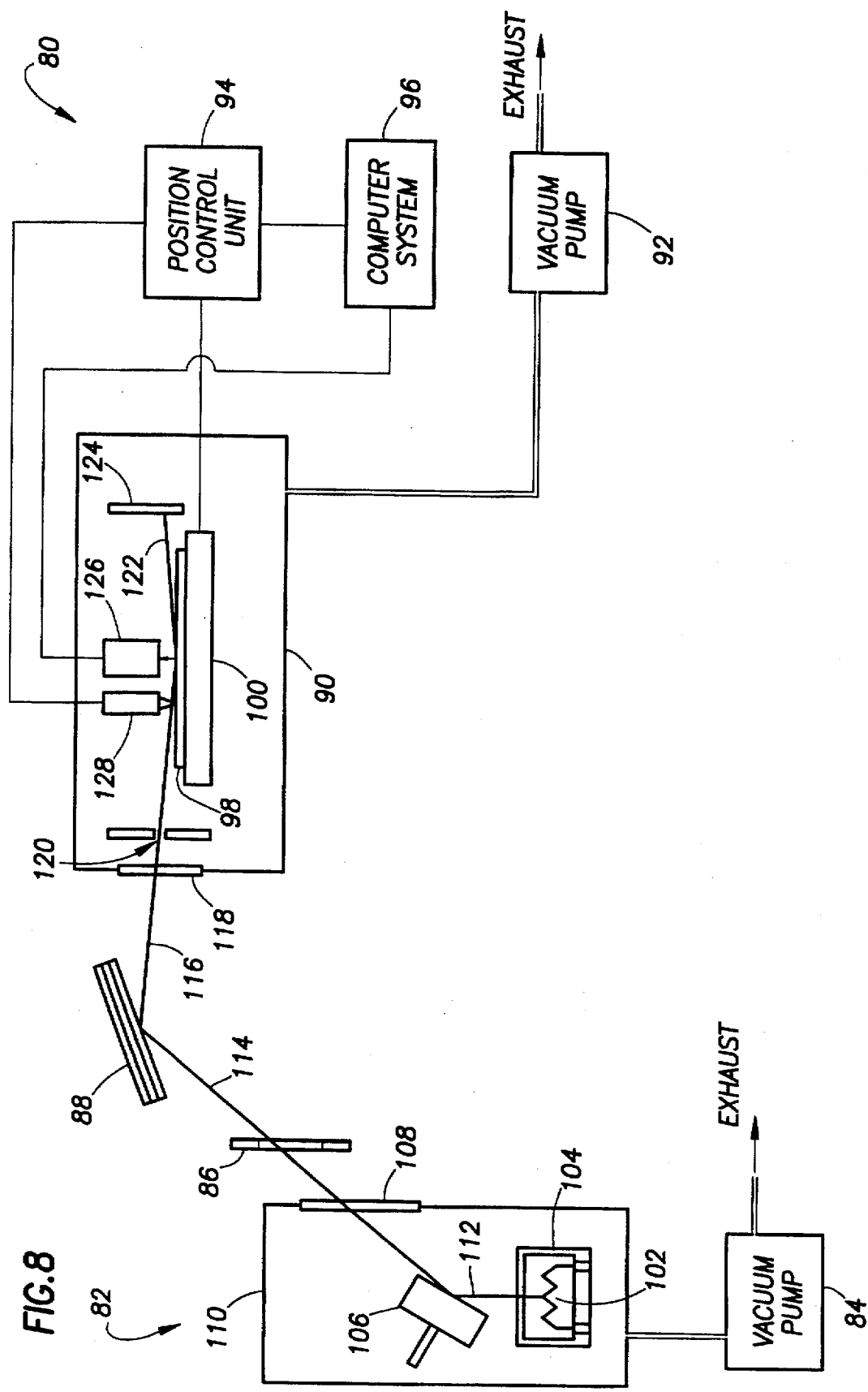
FIG. 8 is a side elevation view of an exemplary embodiment of an apparatus for detecting the relative locations and elemental compositions of particles on the surface of a semiconductor wafer.

FIG. 8 is a side elevation view of an exemplary embodiment of an apparatus 80 for detecting the relative locations and elemental compositions of particles on the surface of a semiconductor wafer. Apparatus 80 includes a high-power X-ray source 82, a first vacuum pump 84, a shutter 86, a multilayer monochromator 88, a sample chamber 90, a second vacuum pump 92, a position control unit 94, and a computer system 96. A planar backside surface of a semiconductor wafer 98 is placed on a flat upper surface of a sample stage 100 located within sample chamber 90, allowing a planar frontside surface of semiconductor substrate 44 to be exposed during analysis.

Due to the nature of TXRF and losses within the apparatus, a high-power X-ray source must be used to produce a relatively large number of X-ray photons per unit time. High-power X-ray source 82 includes a tungsten filament 102, a cathode 104, a rotating anode 106 located within a chamber 110. Chamber 110 is coupled to an inlet port of first vacuum pump 84. First vacuum pump 84 is used to evacuate substantially all of the air molecules from within chamber 110 before and during operation in order to reduce absorption of long wavelength X-ray photons within chamber 110. During operation, an electric current is passed through tungsten filament 102 so as to heat tungsten filament 102 to incandescence. In this state, tungsten filament 102 gives off electrons through the process of thermionic emission. Disc-shaped rotating anode 106 is caused to rotate about an axis perpendicular to its major planar faces, and is held at ground potential during operation. Cathode 104 is charged to a highly negative potential in reference to rotating anode 106, An electron beam 112 is formed as electrons are accelerated toward rotating anode 106 in the electric field generated between cathode 104 and rotating anode 106. As the highly accelerated electrons strike electrons within atoms of rotating anode 106 and lose kinetic energy, X-ray photons are emitted from rotating anode 106 and exit through a beryllium window 108 located in a wall of chamber 110. The walls of chamber 110 are typically made of thick metal in order to prevent X-ray photon penetrations thus X-ray photons may only escape chamber 110 through beryllium window 108.

The one or more materials comprising rotating anode 106 are chosen such that X-ray photons with sufficient energy (i.e., sufficiently short wavelengths) are produced which are able to cause atoms of elements of interest located on and just under the surface of semiconductor wafer 98 to emit secondary X-ray photons. Suitable materials include gold, tungsten, molybdenum, and chromium.

A relatively large number of electrons bombard rotating anode 106 per unit of time, and a great deal of heat energy is generated within rotating anode 106 during operation. If this heat energy is not dissipated rapidly, the anode material will melt. Rotating anode 106 is caused to rotate about an axis perpendicular to its major planar surfaces as to continuously change the area of the surface being bombarded by electrons, thus allowing the resulting heat energy to be dissipated within the mass of the anode. This prevents melting of the anode material in the relatively small area where electron beam 112 strikes rotating anode 106.

The X-ray photons produced by high-power X-ray source 82 have different energy levels and corresponding wavelengths. Thus primary X-ray photons exiting X-ray source 82 form a polychromatic primary X-ray beam 114. Multilayer monochromator 88 is aligned to receive polychromatic primary X-ray beam 114. Shutter 86 positioned between X-ray source 82 and multilayer monochromator 88 passes polychromatic primary X-ray beam 114 when in an open position, and stops polychromatic primary X-ray beam 114 when in a closed position. Multilayer monochromator 88 is configured to receive polychromatic primary X-ray beam 114 and to strongly reflect X-ray photons with a certain wavelength (or corresponding energy level), producing a monochromatic primary X-ray beam 116.

Multilayer monochromator 88 may be a crystal structure made up of many alternating layers of heavy and light elements (e.g., tungsten and carbon). Such multilayer crystals are also called multilayer mirrors. Each layer of a typical multilayer crystal is only a few atoms thick, and has an index of refraction which is different from the other layer. When an incident polychromatic X-ray beam strikes a planar surface of a multilayer crystal at an angle, a small fraction of the incident X-ray beam is reflected at a planar upper surface of the multilayer crystal and at each interface between alternating layers. Reflected X-ray photons which are in phase and reinforce each other form a strongly-reflected monochromatic X-ray beam. Contributions from reflected X-ray photons which are not in phase interfere with one another, largely canceling each other out. The angle of incidence formed between incident polychromatic primary X-ray beam 114 and the planar upper surface of multilayer monochromator 88 is adjusted to produce a monochromatic primary X-ray beam 116 made up of primary X-ray photons with a given wavelength (or corresponding energy level.

Substantially all of the air molecules within sample chamber 90 are evacuated prior to and during operation using vacuum pump 92 in order to reduce absorption of long wavelength X-ray photons within sample chamber 90. Monochromatic primary X-ray beam 116 enters sample chamber 90 through a beryllium window 118 in a wall of sample chamber 90. Once inside sample chamber 90, a portion of monochromatic primary X-ray beam 116 passes through an aperture 120 which limits the cross-sectional area of monochromatic primary X-ray beam 116. Monochromatic primary X-ray beam 116 is thus redefined as it passes through aperture 120, and aperture 120 determines the size and shape of the region on the frontside surface of semiconductor wafer 98 where primary X-ray photons making up monochromatic primary X-ray beam 116 strike the surface of semiconductor wafer 98 (i.e., the exposed region).

In keeping with TXRF techniques described above, an angle of incidence formed between monochromatic primary X-ray beam 116 and the planar frontside surface of semiconductor wafer 98 is very small, typically less than 0.2 degree. At such angles of incidence, almost all of the primary X-ray photons making up monochromatic primary X-ray beam 116 and striking the exposed frontside surface of semiconductor wafer 98 are reflected away from the surface, forming a reflected primary X-ray beam 122. A beam stop 124 absorbs X-ray photons making up reflected primary X-ray beam 122.

Atoms of elements on and just under the region of the frontside surface of semiconductor wafer 98 exposed to primary X-ray photons making up monochromatic primary X-ray beam 116 absorb a fraction of the incident primary X-ray photons and emit characteristic secondary X-ray photons. An X-ray detector array 126 positioned directly above and in close proximity to (i.e., adjacent to) the exposed region of the frontside surface of semiconductor wafer 98 receives the characteristic secondary X-ray photons, in addition to a relatively small number of scattered primary X-ray photons.

X-ray detector array 126 includes two or more separate X-ray detectors laterally displaced from one another and arranged to detect the energy levels and relative positions of secondary X-rays emitted by atoms of elements on and just under the exposed region of the frontside surface of semiconductor wafer 98. X-ray detector array 126 is preferably an electronic area image sensor including a two-dimensional array of photosensor elements formed upon a monolithic substrate as described above. Each photosensor element is thus an X-ray detector. An electronic area image sensor functioning as X-ray detector array 126 produces a train of output signals comprising the outputs of each X-ray detector in the array. A computer system 96 is coupled to receive and store the train of output signals produced by X-ray detector array 126.

In order to facilitate the loading and unloading of semiconductor wafer 98 from sample stage 100, and to allow X-ray detector array 126 to be positioned in close proximity to an exposed region of the frontside surface of semiconductor wafer 98 during operation, X-ray detector array 126 and sample stage 100 move relative to one another. In a preferred embodiment, X-ray detector array 126 remains stationary, and sample stage 100 is configured to move relative to X-ray detector array 126 such that all areas of the frontside surface of semiconductor wafer 98 may be positioned directly under X-ray detector array 126 during operation. Sample stage 100 is thus moveable within physical limits along three orthogonal axes x, y, and z, where the x and y axes are in the horizontal plane and the z axis is normal to the horizontal plane.

A displacement sensor 128 attached to X-ray detector array 126 allows precise and automatic positioning of X-ray detector array 126 above the exposed region of the frontside surface of semiconductor wafer 98 during operation. Displacement sensor 128 produces an output displacement signal which is proportional to the distance between a planar sensing surface of X-ray detector array 126 and the planar frontside surface of semiconductor wafer 98. Suitable displacement sensors use incident and reflected light or sound to determine the displacement between two surfaces.

A position control unit 94 is coupled to receive the displacement signal produced by displacement sensor 128, along with a desired sample stage position signal produced by computer system 96, and is configured to produce a sample stage position control signal derived from both the displacement signal and the desired sample stage position signal. Sample stage 100 is coupled to receive the sample stage position control signal produced by position control unit 94, and is configured to position semiconductor wafer 98 relative to X-ray detector array 126 based upon the sample stage position control signal.

Figure 9:
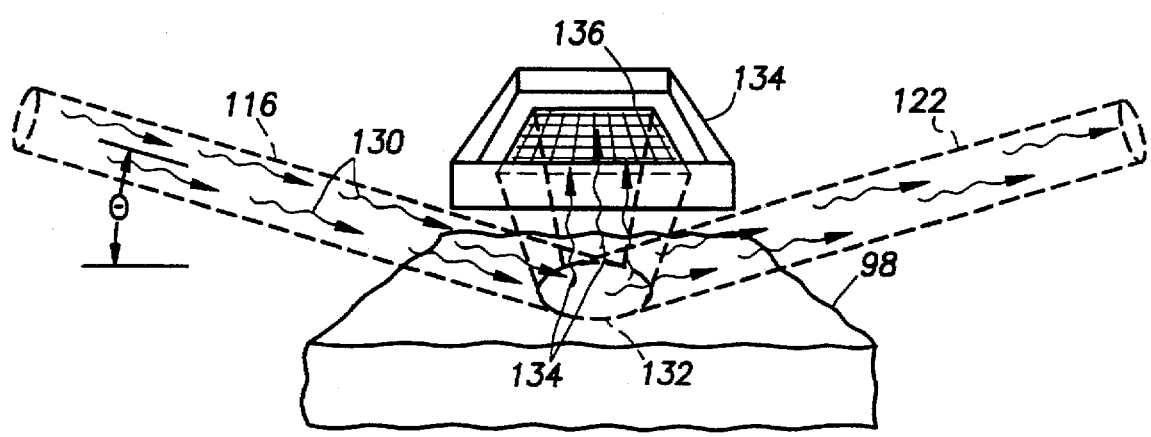
FIG. 9 is a perspective view of a portion of a frontside surface of a semiconductor wafer undergoing analysis using the apparatus of FIG. 8.

FIG. 9 is a perspective view of a portion of the frontside surface of semiconductor wafer 98 undergoing analysis using apparatus 80. As mentioned above, the angle of incidence formed between monochromatic primary X-ray beam 116 and the planar frontside surface of semiconductor wafer 98 is very small, typically less than 0.2 degree. Almost all primary X-ray photons 130 making up monochromatic primary X-ray beam 116 strike the exposed region 132 of the frontside surface of semiconductor wafer 98 and are reflected away, forming reflected primary X-ray beam 122. Atoms of elements on and just under the exposed region 132 of the frontside surface of semiconductor wafer 98 absorb a fraction of the incident primary X-ray photons 130 and emit characteristic secondary X-ray photons 134. In a preferred embodiment, the X-ray detector array positioned directly above and in close proximity to the exposed region 132 of the frontside surface of semiconductor wafer 98 includes an electronic area image sensor 134 with an active sensing area 136 defined by a two-dimensional array of photosensor elements. Each photosensor element is an X-ray detector, and may receive characteristic secondary X-ray photons 134 emitted by the atoms of elements on and just under the exposed region 132 of the frontside surface of semiconductor wafer 98.

Electronic image sensor 134 is positioned in close proximity to the exposed region 132 of the frontside surface of semiconductor wafer 98, typically about 2.0 mm above exposed region 132. At such close spacings, it is believed that the probability that a secondary X-ray photon emitted by a small particle on or just under the surface in the exposed region is incident upon a given photosensor element in the array is inversely proportional to the distance between the particle and the photosensor element. Thus a secondary X-ray emitted by a particle is most likely to be incident upon the nearest photosensor element in the array. The relative location of the secondary X-ray source within the exposed region may thus be determined from the relative location of the receiving photosensor element within the array. In addition, the magnitude of the output signal associated with the photosensor element is linearly proportional to the energy of the secondary X-ray photon incident upon and absorbed within the confines of the photosensor element.

In the preferred embodiment described above, X-ray detector array 126 is an electronic area image sensor which produces a train of output signals comprising the outputs of each X-ray detector in the array. The output signals are typically analog voltage levels. Computer system 96 includes an analog-to-digital converter which receives the train of analog output voltages produced by X-ray detector array 126. The analog-to-digital converter translates an analog output voltage produced by an X-ray detector to a representative digital number. Each digital number produced by the analog-to-digital converter is linearly proportional to the corresponding analog output voltage. Computer system 96 also includes a memory subsystem with storage locations used to store the digital numbers corresponding to the analog output voltages produced by each X-ray detector.

As mentioned above, the analog output voltage of each X-ray detector making up X-ray detector array 126 is linearly proportional to the energy E of an incident X-ray photon. A digital number DN produced by the analog-to-digital converter of computer system 96 is also linearly proportional to a corresponding analog output voltage, thus:

$$DN = k \cdot E$$

where k is a constant of proportionality. A calibration operation is preferably performed in order to determine the value of constant k. For example, X-ray detector array 126 may be exposed to an $^{55}$Fe source known to emit X-ray photons with energies of 5.9 keV and 6.5 keV. The exposure time is kept short enough to ensure that most X-ray detectors in X-ray detector array 126 absorb only a single X-ray photon. Following exposure, the analog output voltage corresponding to each X-ray detector is converted to a digital number as described above. A minimum and a maximum digital number produced by the conversions define a range of the digital numbers. The range of the digital numbers is divided into a manageable number of equally-sized segments (e.g., 250). The digital number associated with the output of each X-ray detector is reviewed, and a count associated with the corresponding segment of the range is incremented. The counts associated with each segment are then plotted versus digital number, forming a histogram representing the frequency distribution of the digital numbers. Two peaks are expected to occur in the plot of counts versus digital number. A first peak is expected to occur in a first segment associated with smaller digital numbers. If the center of the first segment is a digital number $DN_1$, then a first estimate $k_1$ of constant k is:

$$k_1 = DN_1/(5.9 \text{ keV})$$

Similarly, a second peak is expected to occur in a second segment associated with larger digital numbers. If the center of the second segment is a digital number $DN_2$, then a second estimate $k_2$ of constant k is:

$$k_2 = DN_2/(6.1 \text{ keV})$$

The two estimates $k_1$ and $k_2$ may be averaged in order to obtain a more accurate estimate of constant k.

Once the system has been calibrated, the relative locations and elemental compositions of one or more particles on or just under the frontside surface of semiconductor wafer 98 in exposed region 132 may be determined as follows. The frontside surface of silicon wafer 98 is exposed to a source of primary X-rays. Secondary X-rays emitted by atoms of elements on or just under the frontside surface are detected by two or more X-ray detectors within X-ray detector array 126. In the preferred embodiment, X-ray detector array 126 is an electronic area image sensor. Prior to data collection and conversion, an expected range of energy levels of detected secondary X-ray photons is defined and divided into equally-sized segments. Following a predetermined exposure time, X-ray detector array 126 produces a train of output voltages corresponding to the number of charge carriers contained within each X-ray detector in the array. The analog-to-digital converter within computer system 96 converts each analog output voltage to a corresponding digital number. Computer system 96 stores the digital number associated with each analog output voltage. Computer system 96 then converts the digital number associated with the output of each X-ray detector to a corresponding energy level. This conversion is carried out by dividing the digital number by the constant k determined during calibration. Following conversion, computer system 96 stores the corresponding energy level. Computer system 96 also increments the contents of a memory location (i.e., a count) associated with a segment of the expected energy range containing the corresponding energy level. Such conversions and incrementing of counts may be accomplished between successive analog-to-digital conversions or following the storage of the digital numbers number associated with the outputs of the X-ray detectors.

Data collections are carried out over fixed time intervals. In the preferred embodiment described above, output signals are not generated as X-ray photons are absorbed by the X-ray detectors. Instead, photosensor elements of an electronic area image sensor accumulate charges generated by X-ray photon absorption during the data collection time interval (i.e., integration period). As a result, in an elemental analysis mode, the length of the data collection time interval must be chosen to ensure that very few photosensor elements receive more than one secondary X-ray photon. The output signals of photosensor elements which receive two or more secondary X-ray photons may correspond to energy levels which exceed the upper limit of the overall detected energy range. Such output signals are typically ignored, and thus do not contribute to the analysis data. After the data collection time interval has elapsed, output signals proportional to the charges accumulated by each photosensor element are produced in sequence at an output node as described above.

Figure 10:
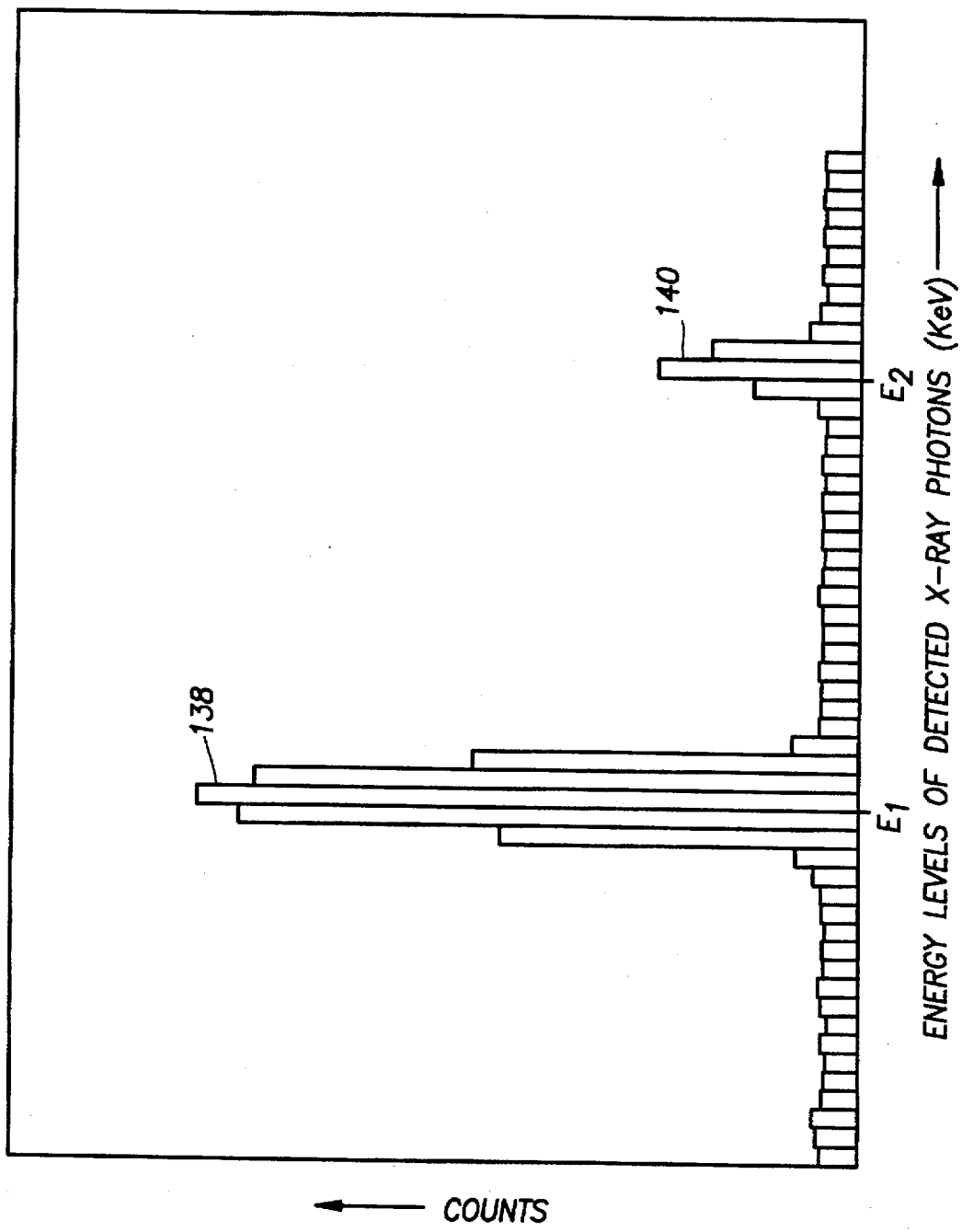
FIG. 10 is a histogram representing the frequency distribution of energy levels of X-ray photons detected during analysis of an exposed region of the frontside surface of the semiconductor wafer.

FIG. 10 is a representative graph of the counts accumulated in computer system 96 versus the energy levels of detected X-ray photons during analysis of an exposed region of a frontside surface of a semiconductor wafer. Such a plot is basically a histogram representing the frequency distribution of the energy levels of detected X-ray photons, and is called a spectral pattern. Peaks in the frequency distribution (i.e., number of counts) occur at predominant characteristic emission energy levels of atoms of elements located on and just under the frontside surface of the semiconductor within the exposed region. The energy levels associated with peaks in the frequency distribution may then be used to identify the elements present on and just under the exposed region of the frontside surface of semiconductor wafer 98 using well-know XRF methods. For example, peaks 138 and 140 in FIG. 10, associated with energy levels $E_1$ and $E_2$, respectively, may be the result of characteristic emissions of atoms of two different elements, or characteristic emissions of atoms of a single element which emit secondary X-ray photons with two different energy levels.

Once the elements present on and just under the frontside surface of semiconductor wafer 98 in exposed region 132 have been identified, the stored digitized output signal information and corresponding energy values may be searched to determine which photosensor elements received secondary X-ray photons emitted by the identified elements. The relative locations of one or more particles within the exposed region are determined from the locations of the corresponding photosensor elements within the array as described above. Thus the preferred embodiment is capable of determining both elemental compositions and relative locations of particles on the surface of a semiconductor wafer. With adequate two-dimensional resolution, the preferred embodiment may also provide information as to the relative sizes of the one or more particles on the surface of the semiconductor wafer.

Figure 11:
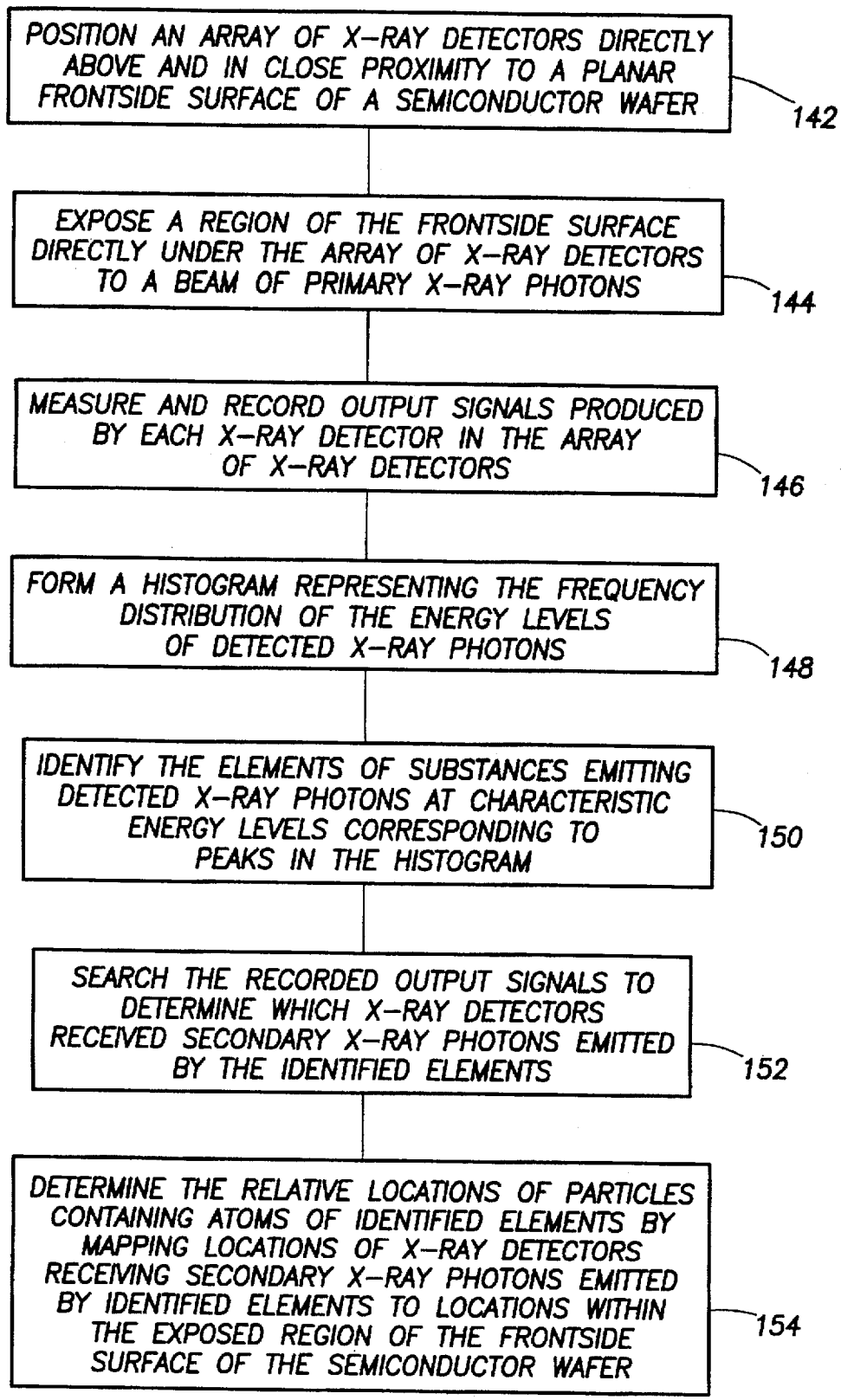
FIG. 11 is a flow chart of a method for determining both elemental compositions and relative locations of particles on the surface of a semiconductor wafer in accordance with the present invention.

FIG. 11 is a flow chart of a method for determining both elemental compositions and relative locations of particles on the surface of a semiconductor wafer in accordance with the present invention. During a first step 142, an array of X-ray detectors is positioned directly above and in close proximity to a planar frontside surface of a semiconductor wafer. A region of the frontside surface directly under the array of X-ray detectors is exposed to a beam of primary X-ray photons during a step 144. During a step 146, output signals produced by each X-ray detector in the array of X-ray detectors are measured and recorded. The output signals are then converted to corresponding energy levels of the detected X-ray photons as described above. An overall detected energy range is divided into many equally-sized segments, and a histogram representing the frequency distribution of the energy levels of detected X-ray photons is formed during a step 148. During a step 150, energy levels corresponding to peaks in the histogram are used to identify elements of particles emitting detected X-ray photons at characteristic energy levels according to well known XRF techniques. The recorded digitized output signals and corresponding energy values are searched to determine the locations of X-ray detectors receiving secondary X-ray photons emitted by the identified elements during a step 152. During a step 154, the relative locations of one or more particles containing atoms of identified elements are determined by mapping the locations of the X-ray detectors receiving secondary X-ray photons emitted by the identified elements to locations within the exposed region of the frontside surface of the semiconductor wafer.

It will be appreciated to those skilled in the art having the benefit of this disclosure that this invention is believed to be an apparatus and method capable of determining the elemental compositions and relative locations of particles on the surface of a semiconductor wafer. Furthermore, it is also to be understood that the form of the invention shown and described is to be taken as exemplary, presently preferred embodiments. Various modifications and changes may be made without departing from the spirit and scope of the invention as set forth in the claims. It is intended that the following claims be interpreted to embrace all such modifications and changes.

What is claimed is:

1. An apparatus for determining the elemental composition and relative location of a particle located upon a surface of a semiconductor wafer, comprising:

an X-ray source configured to produce a plurality of primary X-ray photons, wherein said plurality of primary X-ray photons forms a primary X-ray beam, and said primary X-ray beam is incident upon the surface of the semiconductor wafer; and a plurality of X-ray detectors laterally displaced in more than one direction, wherein each of said plurality of X-ray detectors is positioned to receive a secondary X-ray photon emitted by at least one atom present within said particle.

2. The apparatus as recited in claim 1, wherein said at least one atom comprises a plurality of atoms.

3. The apparatus as recited in claim 2, wherein said plurality of atoms are associated with different elements.

4. The apparatus as recited in claim 1, wherein each of said plurality of X-ray detectors is configured to produce an output signal, wherein said output signal is proportional to an energy level of said secondary X-ray photon.

5. The apparatus as recited in claim 1, wherein the primary X-ray beam is incident upon an exposed region of the surface of the semiconductor wafer, the particle is located within the exposed region, and the plurality of X-ray detectors is positioned adjacent to the exposed region.

6. The apparatus as recited in claim 1, wherein said plurality of X-ray detectors is arranged to allow two-dimensional resolution of detected secondary X-ray photons emitted by atoms of elements on the surface of the semiconductor wafer.

7. The apparatus as recited in claim 1, wherein an angle of incidence formed between the primary X-ray beam and the surface of the semiconductor wafer, measured in a plane containing the primary X-ray beam and normal to the surface of the semiconductor wafer, is less than 0.2 degree.

8. The apparatus as recited in claim 1, wherein the X-ray source comprises a rotating anode.

9. The apparatus as recited in claim 8, wherein the rotating anode comprises tungsten.

10. The apparatus as recited in claim 1, wherein said plurality of X-ray detectors comprises an electronic area image sensor including a plurality of photosensor elements arranged to form a two-dimensional array upon a monolithic semiconductor substrate.

11. An apparatus for determining the elemental composition and relative location of a particle located upon a surface of a semiconductor wafer, comprising:

an X-ray source configured to produce a beam of polychromatic primary X-ray photons;

a multilayer monochromator aligned to receive said beam of polychromatic primary X-ray photons and configured to produce a beam of monochromatic primary X-ray photons, wherein said beam of monochromatic primary X-ray photons is incident upon the surface of the semiconductor wafer;

an X-ray detector array comprising a plurality of laterally displaced X-ray detectors, wherein each of said plurality of X-ray detectors is (i) positioned to receive a secondary X-ray photon emitted by at least one atom present within said particle, and (ii) configured to produce a detector output signal in response to said secondary X-ray photon;

a displacement sensor configured to produce a displacement signal reflecting the distance between the surface of the semiconductor wafer and the X-ray detector array;

a position control unit coupled to receive said displacement signal and configured to produce a position control signal;

a sample stage upon which the semiconductor wafer is placed, wherein the sample stage is coupled to receive said position control signal and configured to position the semiconductor wafer relative to the incident beam of monochromatic primary X-ray photons in response to the position control signal; and a computer system coupled to receive the detector output signal produced by each of said plurality of X-ray detectors.

12. The apparatus as recited in claim 11, wherein said at least one atom comprises a plurality of atoms.

13. The apparatus as recited in claim 12, wherein said plurality of atoms are associated with different elements.

14. The apparatus as recited in claim 11, wherein the detector output signal produced by each of said plurality of X-ray detectors is proportional to an energy level of said secondary X-ray photon.

15. The apparatus as recited in claim 11, wherein the beam of monochromatic primary X-ray photons is incident upon an exposed region of the surface of the semiconductor substrate, the particle is located within the exposed region, and the X-ray detector array is positioned adjacent to the exposed region.

16. The apparatus as recited in claim 11, wherein an angle of incidence formed between the incident beam of monochromatic primary X-ray photons and the surface of the semiconductor wafer, measured in the plane containing the beam of monochromatic X-ray photons and normal to the surface of the surface of the semiconductor wafer, is less than 0.2 degree.

17. The apparatus as recited in claim 11, wherein the X-ray source comprises a rotating anode.

18. The apparatus as recited in claim 17, wherein the rotating anode comprises tungsten.

19. The apparatus as recited in claim 11, wherein said plurality of X-ray detectors comprises an electronic area image sensor including a plurality of photosensor elements arranged to form a two-dimensional array upon a monolithic semiconductor substrate.

20. The apparatus as recited in claim 11, further comprising a sample chamber containing the X-ray detector array, the displacement sensor, and the sample stage, and wherein substantially all of the air molecules within the sample chamber are evacuated prior to and during use.

21. A method for determining the elemental composition and relative location of a particle located upon a surface of a semiconductor wafer, comprising the steps of:

positioning an array of X-ray detectors adjacent to the surface of the semiconductor wafer, wherein the array of X-ray detectors comprises a plurality of laterally displaced X-ray detectors, and each of the plurality of X-ray detectors is (i) oriented to receive a secondary X-ray photon emitted by at least one atom present within said particle, and (ii) configured to produce an output signal in response to said secondary X-ray photon;

exposing the surface of the semiconductor wafer to a beam of primary X-ray photons;

measuring and recording the output signal produced by each of the plurality of X-ray detectors comprising the array of X-ray detectors;

converting the recorded output signals to corresponding energy levels of detected X-ray photons;

forming a histogram representing the frequency distribution of the energy levels of detected X-ray photons;

using the characteristic energy levels corresponding to peaks in the histogram to identify the elemental composition of the particle;

searching the recorded output signals and the corresponding energy levels to determine the relative locations of X-ray detectors receiving secondary X-ray photons emitted by elements comprising the particle within the array of X-ray detectors; and determining the relative location of the particle by mapping the relative locations of X-ray detectors receiving secondary x-ray photons emitted by elements comprising the particle to corresponding locations on the surface of the semiconductor wafer.

22. The method as recited in claim 21, wherein said at least one atom comprises a plurality of atoms.

23. The method as recited in claim 22, wherein said plurality of atoms are associated with different elements.

24. The method as recited in claim 21, wherein the output signal produced by each of said plurality of X-ray detectors is proportional to an energy level of said secondary X-ray photon.

25. The method as recited in claim 21, wherein the X-ray detectors comprising the array of X-ray detectors are arranged to allow two-dimensional resolution of the detected secondary X-ray photon emitted by the atom of the element present within the particle.

26. The method as recited in claim 25, wherein said plurality of X-ray detectors comprises an electronic area image sensor including a plurality of photosensor elements arranged to form a two-dimensional array upon a monolithic semiconductor substrate.

27. The method as recited in claim 21, wherein the beam of primary X-ray photons is incident upon an exposed region of the surface of the semiconductor wafer, the particle is located within the exposed region, and the X-ray detector array is positioned adjacent to the exposed region.

28. The method as recited in claim 21, wherein an angle of incidence formed between the incident beam of primary X-ray photons and the surface of the semiconductor wafer, measured in the plane containing the beam of primary X-ray photons and normal to the surface of the semiconductor wafer, is less than 0.2 degree.

* * * * *